(12) United States Patent
Kumar et al.

(10) Patent No.: US 7,045,618 B2
(45) Date of Patent: May 16, 2006

(54) CEFPODIXIME PROXETIL

(75) Inventors: Yatendra Kumar, Haryana (IN); Kaptan Singh, Uttar Pradesh (IN); Rakesh Kumar Arora, Haryana (IN)

(73) Assignee: Ranbaxy Laboratories Limited, Haryana (IN)

( * ) Notice: Subject to any disclaimer, the term of this patent is extended or adjusted under 35 U.S.C. 154(b) by 20 days.

(21) Appl. No.: 10/469,330

(22) PCT Filed: Feb. 27, 2002

(86) PCT No.: PCT/IB02/00588

§ 371 (c)(1),
(2), (4) Date: Dec. 18, 2003

(87) PCT Pub. No.: WO02/068429

PCT Pub. Date: Sep. 6, 2002

(65) Prior Publication Data

US 2004/0092734 A1    May 13, 2004

(30) Foreign Application Priority Data

Feb. 27, 2001 (IN) .......................... 191/DEL/2001

(51) Int. Cl.
*C07D 501/34* (2006.01)
(52) U.S. Cl. ...................................... 540/220; 540/228
(58) Field of Classification Search .................. 540/220
See application file for complete search history.

(56) References Cited

U.S. PATENT DOCUMENTS

| 4,482,710 A | 11/1984 | Fujimoto et al. ............. 544/28 |
| 4,486,425 A | 12/1984 | Nakao et al. ................ 424/246 |
| 5,461,043 A | 10/1995 | Fischer et al. .............. 514/202 |
| 6,639,068 B1 * | 10/2003 | Lee et al. .................... 540/228 |
| 2002/0065262 A1 * | 5/2002 | Greil et al. ................. 514/202 |
| 2005/0020561 A1 * | 1/2005 | Kumar et al. ............... 514/202 |

FOREIGN PATENT DOCUMENTS

| EP | 0 029 557 | 3/1981 |
| WO | WO 99/35149 | 7/1999 |
| WO | WO 00/66594 | 11/2000 |
| WO | WO 01/09143 | 2/2001 |
| WO | WO 01/34611 | 5/2001 |
| WO | WO 01/87893 | 11/2001 |

\* cited by examiner

*Primary Examiner*—Mark L. Berch
(74) *Attorney, Agent, or Firm*—Jayadeep R. Deshmukh, Esq.; George E. Heibel, Esq.

(57) ABSTRACT

The present invention relates to an improved and cost effective process for the industrial manufacture of cefpodoxime proxetil. More specifically, the present invention relates to the preparation of cefpodoxime proxetil of high purity and yield. The process comprises a) dissolving impure cefpodoxime proxetil or adding a solution containing cefpodoxime proxetil into a polar organic solvent or mixture(s) thereof, optionally reducing the solvent by concentration, and adding into a non-polar organic solvent or mixture(s) thereof to precipitate the solid; and b) dissolving the solid obtained from the above step into water-miscible polar organic solvent, optionally reducing the solvent by concentration, adding it into water to obtain the pure cefpodoxime proxetil.

12 Claims, No Drawings

CEFPODIXIME PROXETIL

FIELD OF THE INVENTION

The present invention relates to an improved and cost effective process for the industrial manufacture of cefpodoxime proxetil. More specifically, the present invention relates to the preparation of cefpodoxime proxetil of high purity and yield.

BACKGROUND OF THE INVENTION

Chemically, cefpodoxime proxetil is 1-isopropoxycarbonyloxyethyl(6R, 7R)-7-[2-(2-aminothiazol-4-yl)-2-(Z)-(methoxyimino)acetamido]-3-(methoxymethyl)-3-cephem-4-carboxylate of Formula I and is disclosed in U.S. Pat. No. 4,486,425.

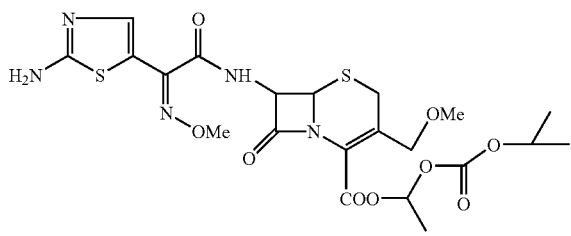

I

Cefpodoxime proxetil is one of the limited class of third generation cephalosporin derivatives which can be administered orally as it is readily adsorbed through the digestive tract and which is then readily hydrolyzed and converted in vivo to the corresponding carboxylic acid which, in turn, shows outstanding antibacterial activity against both gram-positive and gram-negative bacteria.

Pharmaceutical compounds are required in highly pure form because of the fear of unknown and potentially harmful effects of impurities. For purposes of patient' safety, it is highly desirable to limit the amount of impurities present in any medicament administered to a patient. This is achieved by either devising a process for or by additional purification steps like chromatography or recrystallization etc. The purity of intermediates and raw materials is essential for obtaining the target pharmaceutical compounds in high yield and purity.

A number of methods have been outlined in U.S. Pat. No. 4,486,425 for the synthesis of the cefpodoxime esters. However, in each of these methods, esterification of the carboxylic acids of the cephem ring results in impurities which have to be removed using silica gel column chromatography, as illustrated in the examples. U.S. Pat. Nos. 4,482,710 and 5,461,043 also illustrate the synthesis of cefpodoxime proxetil using methods outlined in U.S. Pat. No. 4,486,425 which employ chromatography after the esterification step to remove impurities and to get pure cefpodoxime proxetil.

PCT application WO 99/35149 describes the preparation of cefpodoxime proxetil with a focus on the adjustment of diastereoisomeric ratio of the two diastereoisomers of cefpodoxime proxetil in the product mixture. Although, the process illustrated in this PCT application does not use chromatographic techniques for isolation of products, the process involves additional steps of protection and deprotection at the amino position of the thiazolyl moiety.

Thus none of the prior art processes are satisfactory for the reasons described above.

SUMMARY OF THE INVENTION

It is an object of the present invention to provide a cost effective and industrially advantageous process for the purification and isolation of the desired syn isomer of cefpodoxime proxetil in high purity and yield thus, obviating the need for chromatography or additional steps of protection and deprotection.

Accordingly, the present invention provides a novel and industrially advantageous process for isolating the pure cefpodoxime proxetil of Formula I

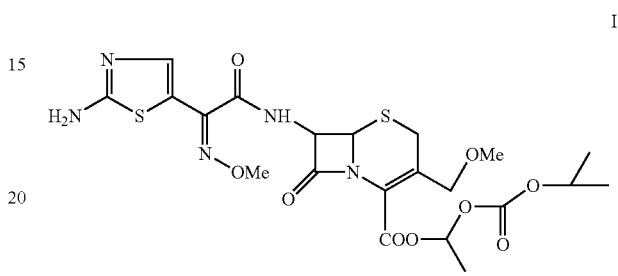

I which removes the common impurities (the Δ²-isomer of Formula II and anti-isomer of Formula III as shown below:

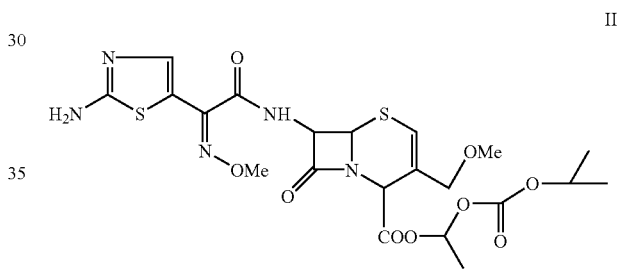

II

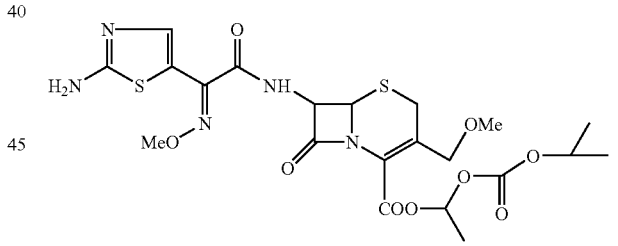

III formed during the esterification reaction. Further, the process of the present invention also has the capabilities to eliminate the other side products formed during the esterification step i.e. the reaction of 1-iodoethylisopropyl carbonate of Formula IV

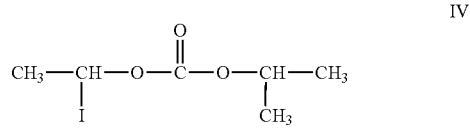

IV with the unprotected amino group of the thiazolyl moiety of cefpodoxime proxetil of Formula I. Thus, the product obtained by following the present process is highly pure without the use of chromatography or without carrying out additional steps of protection and deprotection.

More specifically, the present invention relates to a process for the purification and isolation of pure cefpodoxime proxetil of Formula I, comprising the steps:

a) dissolving impure cefpodoxime proxetil or adding a solution containing cefpodoxime proxetil into a polar organic solvent or mixture(s) thereof, optionally reducing the solvent by concentration, and adding into a non-polar organic solvent or mixture(s) thereof to precipitate the solid;

b) dissolving the solid obtained from the above step into water-miscible polar organic solvent, optionally reducing the solvent by concentration, adding it into water to obtain the pure cefpodoxime proxetil.

The scope of the present invention also covers the process for obtaining the pure cefpodoxime proxetil wherein the order of purification and isolation i.e. steps (a) and (b) is reversed.

In turn, cefpodoxime proxetil of Formula I may be obtained in situ by reacting 7-(2-(2-aminothiazol-4-yl)-2-methoxy-3-cephem carboxylic acid i.e. cefpodoxime acid (prepared as per the general process described in EP 29557) of Formula V or salt thereof,

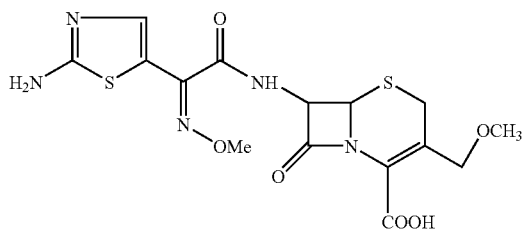

V with 1-iodoethyl isopropylcarbonate of Formula IV,

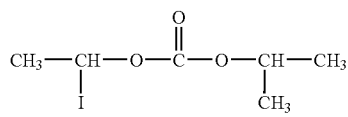

IV in the presence of a base which is followed by the purification and isolation of pure cefpodoxime proxetil as per the steps (a) and (b), above.

In the meaning of the present invention, the term "water-miscible" shall refer to organic solvents which show essentially unlimited, preferably 100% miscibility with water. The polar organic solvents may have limited water miscibility and the term "limited miscibility" shall also include water-immiscible organic solvents.

Example for water-miscible organic solvents include lower alcohols such as methanol, ethanol and isopropanol; lower alkyl ketones such as acetone, lower alkyl glycol ethers such as methyl glycol; dipolar aprotic solvents such as N,N-dimethyl formamide (DMF), N,N-dimethylacetamide (DMA) and dimethyl sulfoxide (DMSO) and cyclic ethers such as tetrahydrofuran, dioxane, or mixture(s) thereof.

Particularly preferred solvents are methanol, ethanol, isopropanol, and acetone.

Examples of polar organic solvents having limited miscibility in water include carboxylic acid esters such as ethyl acetate, higher alkyl ketones such as methylisobutyl ketone; chlorinated hydrocarbons, such as dichloromethane or mixture(s) thereof. Particularly preferred solvents are ethyl acetate and dicholoromethane. Suitable non-polar organic solvents include hydrocarbons such as hexane, xylene; higher alkyl ethers such as diisopropyl ether, cyclic hydrocarbons such as cyclohexane, or mixture(s) thereof. Particularly preferred are diisopropyl ether and cyclohexane.

It has been observed that slow, preferably dropwise, addition of the solution into a well stirred non-polar solvent or water (in first and second precipitation, respectively) gives the desirable purity of the product while adding the solution all at once, may result in lumps or a gummy product.

Cefpodoxime acid of Formula V used in the esterification reaction may be in the form of a salt, for example, an alkali metal salt, such as sodium or potassium salt, an ammonium salt or salt with nitrogen containing bases, such as triethylamine and dicyclohexylamine.

The base may be selected from the group consisting of inorganic such as potassium carbonate, sodium carbonate and sodium bicarbonate, or organic such as triethylamine, dicyclohexylamine, 1,8-diazabicyclo[5,4.0]undec-7-ene (DBU) and N,N-dimethylaniline or a mixture thereof. If the starting compound of Formula V is in the form of a carboxylic acid salt such as sodium or potassium, it may be used in the reaction as such, without any base.

The reaction is performed in the presence of a solvent. Suitable solvents include dimethylformamide, dimethylacetamide, dimethylsulphoxide, tetrahydrofuran, dichloromethane, ethylacetate, acetonitrile or mixture(s) thereof. The reaction is conducted at ambient temperature or with cooling, preferably at −10 to 0° C.

The reaction mixture containing cefpodoxime proxetil in situ is then poured in to a polar organic solvent having limited miscibility or solubility in water and washed successively with aqueous solutions of hydrochloric acid, sodium bicarbonate, sodium thiosulphate and sodium chloride in sequence.

The washed organic layer is concentrated and is then added into a non-polar organic solvent to accomplish the first precipitation.

The product is further purified by dissolving the product in a water miscible and optionally subjecting it to carbon treatment followed by partial concentration and addition of the concentrated layer into water to effect the second precipitation and obtain highly pure cefpodoxime proxetil. The separated solid is filtered and dried.

The compounds of Formula I may be obtained in the form of acid addition salts with pharmaceutically acceptable acids, for example inorganic acids such as hydrochloric acid, sulfuric acid and phosphoric acid or organic acids such as malonic acid, oxalic acid and tartaric acid.

DETAILED DESCRIPTION OF THE INVENTION

In the following section one preferred embodiment is described by way of example to illustrate the process of this invention. However, it is not intended in any way to limit the scope of the present invention.

EXAMPLE

Preparation of Cefpodoxime Proxetil in Situ 10 g of (6R,7R) 7-[2-(2-aminothiazol-4-yl)-2-methoxy-imino-acetamido]-3-(methoxymethyl)3-cephem-4-carboxylic acid was added to 60 ml of N,N-dimethylacetamide and the mixture was cooled to −8° C. 1,8-diazabicyclo[5,4.0]undec-7-ene (DBU) (3.33 g) was added followed by addition of 1-iodoethyl isopropyl carbonate (5.85 g) at −8 to −5° C. The reaction mixture was stirred for 45 min at the same temperature.

The reaction mixture thus obtained was poured into ethyl acetate (300 ml) followed by the addition of water (300 ml) at 20–22° C. The mixture was stirred for 10 min and the organic layer was separated. The organic layer was then washed successively with aqueous hydrochloric acid, aqueous sodium thiosulphate, and finally with aqueous sodium chloride.

Purification and Isolation of Pharmaceutical Grade Cefpodoxime Proxetil

Step—(a)

The ethyl acetate layer as obtained above was concentrated to about 40 ml at 30–35° C. under reduced pressure and added to cyclohexane (300 ml) under stirring at 25° C during about 30 minutes. The precipitated solid was then filtered and washed with cyclohexane.

Step (b)

The wet product from Step (a) was added to methanol (40 ml) at room temperature to obtain a solution and was concentrated at 30–35° C. under reduced pressure to about 30 ml. It was then added to water (180 ml) in 15 minutes at 20–25° C. to obtain a solid which was filtered and washed with a cold mixture of methanol and water (1:6 v/v, 20 ml). The filtered solid was dried to obtain 9 g of pure cefpodoxime proxetil. (Diastereoisomeric mixture ratio B/A+B=0.52 where B is the more polar isomer, Assay: 98%).

While the present invention has been described in terms of its specific embodiments, certain modifications and equivalents will be apparent to those skilled in the art and are intended to be included within the scope of the present invention.

The invention claimed is:

1. A process for the purification and isolation of pure cefpodoxime proxetil of Formula I, or pharmaceutically acceptable salts thereof,

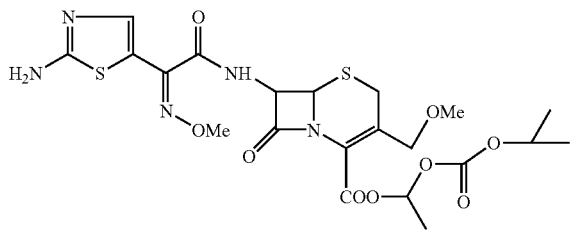

I comprising:
(a) dissolving impure cefpodoxime proxetil or adding a solution containing cefpodoxime proxetil into a polar organic solvent or mixture(s) thereof, optionally reducing the solvent by concentration, and adding into a non-polar organic solvent or mixture(s) thereof to precipitate the solid; and
(b) dissolving the solid obtained from the above step into water-miscible polar organic solvent, optionally reducing the solvent by concentration, and adding into water to obtain the pure cefpodoxime proxetil.

2. The process according to claim 1, wherein cefpodoxime proxetil is obtained by reacting cefpodoxime acid of Formula V,

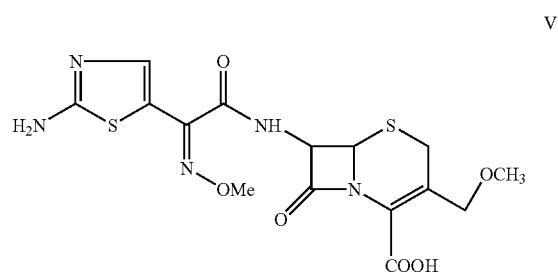

V or a salt thereof with 1-iodoethyl isopropyl carbonate of Formula IV,

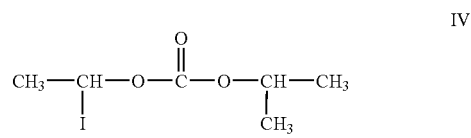

IV optionally in the presence of a base.

3. The process according to claim 1 or 2, wherein the solution obtained after dissolving cefpodoxime proxetil or by adding a solution containing cefpodoxime proxetil into a polar organic solvent is washed with aqueous acidic and/or basic solution.

4. The process according to claim 1 or 2, wherein the polar organic solvent has limited miscibility in water.

5. The process according to claim 4 wherein the polar organic solvent having limited miscibility in water is ethyl acetate or dichloromethane.

6. The process according to claim 1 or 2 wherein the non-polar organic solvent is diisopropyl ether or cyclic hydrocarbon.

7. The process according to claim 6 wherein the cyclic hydrocarbon is cyclohexane.

8. The process according to claim 1 or 2 wherein the water miscible organic solvent is methanol, ethanol, isopropanol, or acetone.

9. The process according to claim 8 wherein the water miscible organic solvent is methanol.

10. The process according to claim 2 wherein the compound of Formula V is a sodium salt of cefpodoxime acid.

11. The process according to claim 2 wherein the base used is selected from the group consisting of potassium carbonate, sodium carbonate, dicyclohexylamine, 1,8-diazabicylco [5.4.0]undec-7-ene (DBU), and mixture(s) thereof.

12. The process according to claim 2, wherein the reaction is performed at −10 to 0° C.

* * * * *

UNITED STATES PATENT AND TRADEMARK OFFICE
CERTIFICATE OF CORRECTION

PATENT NO. : 7,045,618 B2 Page 1 of 1
APPLICATION NO. : 10/469330
DATED : May 16, 2006
INVENTOR(S) : Yatendra Kumar et al.

It is certified that error appears in the above-identified patent and that said Letters Patent is hereby corrected as shown below:

Please Insert
1. Title Page, Item [54] - "CEFPODIXIME" should read --CEFPODOXIME--
2. Column 1, Line 1 - "CEFPODIXIME" should read --CEFPODOXIME--

Signed and Sealed this

Twenty-sixth Day of December, 2006

JON W. DUDAS
*Director of the United States Patent and Trademark Office*